United States Patent [19]

Carpenter

[11] Patent Number: 4,778,247

[45] Date of Patent: Oct. 18, 1988

[54] MOLDED OBJECTIVE HEAD FOR FIBERSCOPES WITH INTEGRAL LENSES

[75] Inventor: George J. Carpenter, Southbridge, Mass.

[73] Assignee: Warner Lambert Technologies, Inc., Southbridge, Mass.

[21] Appl. No.: 104,818

[22] Filed: Oct. 5, 1987

Related U.S. Application Data

[63] Continuation of Ser. No. 607,035, May 4, 1984, abandoned.

[51] Int. Cl.$^4$ .................. G02B 23/26; A61B 1/00; F21V 7/04
[52] U.S. Cl. .................. 350/96.26; 350/96.10; 350/96.25; 128/4; 128/6; 362/32
[58] Field of Search ............. 350/96.10, 96.20, 96.24, 350/96.25, 96.26, 96.34, 96.27, 96.28; 362/32; 128/4, 6; 264/1.1, 1.5, 1.6, 2.1, 2.5

[56] References Cited

U.S. PATENT DOCUMENTS

| | | | |
|---|---|---|---|
| 3,649,098 | 3/1972 | Suverison | 350/96.18 |
| 3,995,934 | 12/1976 | Nath | 128/6 X |
| 4,266,534 | 5/1981 | Ogawa | 128/6 |
| 4,281,646 | 8/1981 | Kinoshita | 128/6 |
| 4,641,635 | 2/1987 | Yabe | 128/6 |
| 4,649,904 | 3/1987 | Krauter et al. | 128/6 |
| 4,667,656 | 5/1987 | Yabe | 128/6 |
| 4,735,194 | 4/1988 | Stiegmann | 128/6 |
| 4,740,047 | 4/1988 | Abe et al. | 350/96.10 X |

Primary Examiner—William L. Sikes
Assistant Examiner—Brian M. Healy
Attorney, Agent, or Firm—Bachman & LaPointe

[57] ABSTRACT

An objective head for a fiberscope fabricated (cast or molded) from optically clear plastic having lenses molded integrally with the head to form a single piece-part and method of fabrication.

7 Claims, 1 Drawing Sheet

MOLDED OBJECTIVE HEAD FOR FIBERSCOPES WITH INTEGRAL LENSES

This is a continuation, of application Ser. No. 607,035 filed May 4, 1984, now abandoned.

BACKGROUND OF THE INVENTION

The present invention deals with fiberscopes useful in medical, veterinary and industrial applications using bundles of optical fibers to illuminate and to transmit images of remotely located objects.

Because of the nature of glass fibers (numerical aperture), it is frequently necessary to utilize a lens or lens system at the distal or objective end of light guide fiber optic bundle to spread light providing illumination for the imaging view.

In most fiberscopes the various light guide and imaging bundles are received and anchored within a metallic element known as an objective head.

The metallic head is machined to provide recesses and appropriate through bores to accommodate fiber bundles and to provide outlets for the usual and customary utility channels such as air, water, suction, biopsy instruments and the like.

The required lenses, usually of glass, are individually manufactured at relatively high cost because of their small size, i.e., 1 to 2 mm. in diameter by 0.75 to 1.0 mm. thick.

These small glass objects are cemented into machined counterbores in the metallic head.

A representative example of prior art is disclosed in U.S. Pat. No. 4,266,534 issued May 12, 1981, to Mototogu Ogawa and assigned on its face to Olympus Optical Co., Ltd., Tokyo, Japan. In this disclosure a variety of lenses 6 are shown cemented to machined counterbores in a metallic objective head.

The problem with prior art lens settings is the risk and the dangerous consequences of a lens falling out of its setting and detaching from the instrument during a critical medical, veterinary or industrial procedure.

Another problem with prior art objective heads is the expense of manufacture.

A still further problem with the prior art device is its ability to conduct electricity. Since various electrical power sources are associated frequently with modern fiberscopes, it has become necessary to provide electrical grounds to insure against injury resulting from random or stray currents transmitted through a metallic head.

SUMMARY OF THE INVENTION

Therefore, it is a primary object of the present invention to provide a novel objective head structure which avoids the risk of having lenses drop out of their settings. There is no need for cement because the lenses are molded integrally with the objective head.

A further object is the provision of a novel method of fabricating an objective head.

A still further feature of the invention is the provision of an inexpensive objective head-lens structure in the form of a single piece-part.

It is a still further object of the invention to provide a dielectric head for a fiberscope thereby precluding the need for an electrical ground.

Molding imaging and light guide lenses integrally with the objective head insures a tight seal protecting the imaging and light systems from moisture encountered during medical procedures or during sterilization.

A fitting for the distal end of a fiberscope embracing certain principles of the present invention may comprise a molded, optically clear plastic objective head, said molded head having recesses for receiving and anchoring at least one light guide fiber optic bundle, at least one imaging fiber optic bundle and at least one lens defining an integral part of the molded plastic head individual to each recess and in close proximity to mating fiber optic bundles, the lenses and the molded head defining a single piece-part.

A method embracing principles of the invention may comprise providing a mold in the desired configuration of the head, placing a core in the mold so that a bottom wall of said recess defines a lens shape, molding the head using optically clear plastic material and removing the core from the molded head thereby creating a molded plastic objective head with an integral lens where said head and said lens define a single piece-part.

Other features and advantages of the invention will become more apparent from an examination of the succeeding specification when read in conjunction with the appended drawings, in which;

DESCRIPTION OF PREFERRED EMBODIMENTS

Figure 1:
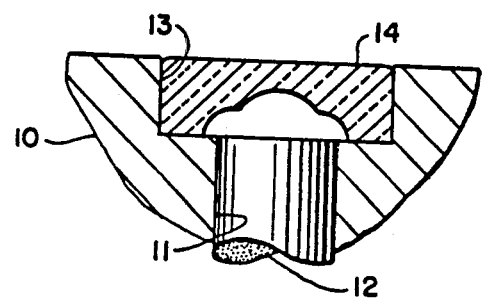
FIG. 1 is a representation of a prior art lens receptacle.

Referring to the drawings and in particular to FIG. 1, a fragmentary view of a prior art device shows a machined metallic sleeve 10 formed with a bore 11 for receiving a fiber optic bundle 12. A machined recess or counterbore 13 provides a receptacle or setting for a lens 14 fabricated as a separate piece-part and cemented in place.

Figure 2:
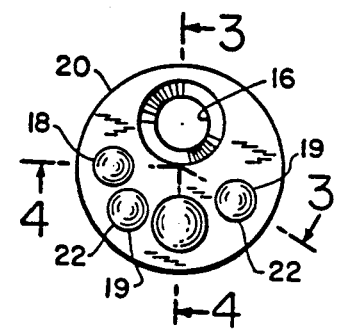
FIG. 2 is a schematic view of an end face of an objective head of the present invention.
Figure 3:
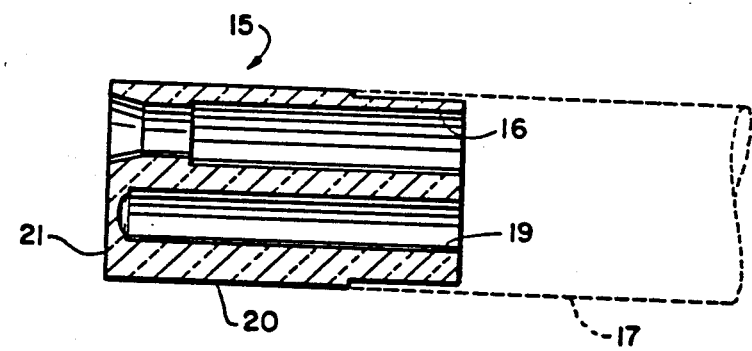
FIG. 3 is a sectional view of FIG. 2 sectioned along the line 3—3.
Figure 4:
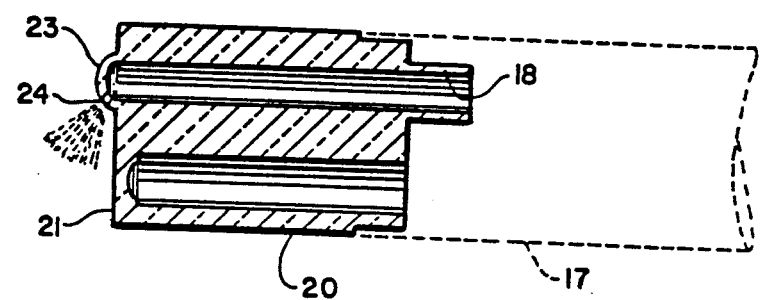
FIG. 4 is a sectional view of FIG. 2 sectioned along the line 4—4.

In contrast, FIGS. 2, 3 and 4 deal with a generally cylindrical unitary member indicated generally by the reference numeral 15 of molded or cast optically clear plastic material such as a polycarbonate resin.

Other suitable resins are acrylics and urethanes.

For purposes of claiming the present invention, the member 15 is termed an objective head.

The head 15 includes a body 20 through bore 16 which communicates with a channel within a flexible shaft 17 of a fiberscope in well-known fashion.

The bore 16 provides a conduit for a biopsy instrument and can be switched selectively to a source of suction while bore 18 communicates with a source of water and air in usual and customary manner.

Bores 19—19 receive and anchor fiber optic bundles (not shown) serving as light guides providing illumination at the face 21 of the head 15 and light is spread over the field of view of the imaging system by light guide lenses 22—22.

Note that the lenses 22—22 are molded or cast integrally with the body 20 defining with the body a single piece-part. These lenses 22—22 also make a seal protecting the light guide fiber optic bundles.

With respect to bore 18 (FIG. 4), note that a rounded protuberance or projection 23 extends slightly beyond the face of the objective head. This protruding structure affords a means for directing air or water in a predetermined direction across the face 21 of the objective head. Air or water, as the case may be, is directed in a predetermined direction by forming one or more orifices such as orifice 24 (FIG. 4) in an appropriate location in the protuberance 23.

Here again, note that the protuberance or projection 23 is molded integrally and defines a single piece-part with the lenses 22—22 and the body 20.

The image bundle received in channel 15 (FIG. 4) is also provided with an integral lens 25. Thus all fiber optic bundles are provided with (1) a safe, cement-free lens and (2) a liquid-tight seal blocking moisture arising from a medical, veterinary or industrial procedure or from sterilization.

The objective head 15 is formed or fabricated by preparing a mold cavity in the desired configuration, inserting in the mold a mold core to define the lens shape, injecting optically clear plastic material into the mold and after the plastic is set removing the core to develop a unitary objective head with "built-in" lens.

If desired, the head exterior may be coated with a film of scratch-resistant material such as Permalite or Duralite (both are trade names for organic silanes) to preserve the integrity of the clarity of the plastic.

It is anticipated that a wide variety of embodiments of the article and the method of the present invention may be devised without departing from the spirit and scope thereof.

What is claimed is:

1. An objective head for an image-transmitting fiberscope useful in medical, veterinary and industrial applications of the type having at the distal or objective end recesses for receiving image and lighting fiber optic bundles and outlet for utility channels such as for air, irrigation, suction and biopsy instruments characterized in that it comprises an optically clear molded plastic structure, free of moving and metallic parts, having at least one recess for receiving and anchoring at least one light guide fiber optic bundle and at least one imaging fiber optic bundle and at least one lens associated with each recess and each fiber optic bundle received therein, the lenses and the head being molded as an integral single piece structure.

2. An objective head according to claim 1 in which the head is formed with at least one utility outlet operable to communicate with a utility channel in a fiberscope.

3. An objective head according to claim 2 in which one utility channel outlet defines a bore open at one end and substantially closed at the opposite end by a protuberance which is an integral part of the head, said protuberance having an orifice located in a predetermined position effective to direct fluid passing through said bore across the face of said head.

4. An objective head according to claim 1 molded from polycarbonate resin.

5. An objective head according to claim 2 molded from polycarbonate resin.

6. An objective head according to claim 3 molded from polycarbonate resin.

7. An objective head according to claim 4 having an exterior coating of transparent optically clear scratch-resistant material.

* * * * *